United States Patent
Pei

(10) Patent No.: US 7,587,243 B1
(45) Date of Patent: Sep. 8, 2009

(54) SYSTEM AND METHOD FOR VERIFYING CAPTURE AND/OR EVENT SENSING DURING MANUAL THRESHOLD EVALUATIONS OF AN IMPLANTABLE CARDIAC STIMULATION DEVICE

(75) Inventor: Xing Pei, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 719 days.

(21) Appl. No.: 11/430,785

(22) Filed: May 8, 2006

(51) Int. Cl.
*A61N 1/362* (2006.01)

(52) U.S. Cl. ...................................... 607/28

(58) Field of Classification Search ............... 607/28
See application file for complete search history.

(56) References Cited

U.S. PATENT DOCUMENTS

| | | | | |
|---|---|---|---|---|
| 4,596,255 A | 6/1986 | Snell et al. | ............. | 600/510 |
| 4,712,555 A | 12/1987 | Thornander et al. | ............. | 607/17 |
| 4,788,980 A | 12/1988 | Mann et al. | ............. | 607/14 |
| 4,791,936 A | 12/1988 | Snell et al. | ............. | 600/510 |
| 4,940,052 A | 7/1990 | Mann et al. | ............. | 607/14 |
| 4,944,298 A | 7/1990 | Sholder | ............. | 607/14 |
| 5,466,254 A | 11/1995 | Helland | ............. | 607/123 |
| 5,716,382 A | 2/1998 | Snell | ............. | 607/30 |
| 5,925,067 A | 7/1999 | Lu | ............. | 607/28 |
| 5,974,341 A | 10/1999 | Er et al. | ............. | 607/31 |
| 6,594,523 B1 | 7/2003 | Levine | ............. | 607/30 |
| 6,738,669 B1 * | 5/2004 | Sloman et al. | ............. | 607/28 |
| 6,768,924 B2 * | 7/2004 | Ding et al. | ............. | 607/28 |
| 6,885,893 B1 * | 4/2005 | Lu | ............. | 607/28 |
| 7,006,869 B2 * | 2/2006 | Bradley | ............. | 607/28 |
| 7,096,065 B2 * | 8/2006 | Conley et al. | ............. | 607/27 |
| 2001/0049542 A1 * | 12/2001 | Florio et al. | ............. | 607/28 |
| 2002/0095190 A1 | 7/2002 | Bornzin et al. | ............. | 607/28 |
| 2004/0230244 A1 * | 11/2004 | Conley et al. | ............. | 607/28 |

FOREIGN PATENT DOCUMENTS

| | | |
|---|---|---|
| EP | 1 222 942 A2 | 7/2002 |
| EP | 1 222 942 A3 | 7/2002 |

\* cited by examiner

*Primary Examiner*—Carl H Layno
*Assistant Examiner*—Yun Haeng Lee

(57) ABSTRACT

A system verifies the occurrence of a cardiac event during a manual evaluation of a pacing and/or sensing parameter of an implantable cardiac stimulation device. The system comprises a template generator that generates an electrogram template standard characterizing the cardiac event, an event marker pattern generator that generates a marker pattern standard representing a desired sequence of cardiac events including the cardiac event, and a sensing circuit that senses cardiac activity to provide an evaluation electrogram signal responsive to evaluation of the pacing and/or sensing parameter. The template generator generates an evaluation electrogram and the event marker pattern generator generates an evaluation marker pattern from the evaluation electrogram signal. A cardiac event verifier verifies the occurrence of the cardiac event when the evaluation electrogram matches the electrogram template standard and the evaluation marker pattern matches the marker pattern standard.

20 Claims, 5 Drawing Sheets

SYSTEM AND METHOD FOR VERIFYING CAPTURE AND/OR EVENT SENSING DURING MANUAL THRESHOLD EVALUATIONS OF AN IMPLANTABLE CARDIAC STIMULATION DEVICE

FIELD OF THE INVENTION

The present invention generally relates to evaluations performed with implantable cardiac stimulation systems. The present invention more particularly relates to sensing and/or capture verification during manual threshold evaluations of an implantable cardiac device.

BACKGROUND OF THE INVENTION

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator.

A pacemaker is comprised of two major components. One component is the device itself which includes pulse generator circuitry that generates the pacing stimulation pulses, other circuitry that senses cardiac activity, and a power cell or battery. The other component is the lead, or leads, having electrodes which electrically couple the pacemaker to the heart. A lead may provide both unipolar and bipolar pacing polarity electrode configurations. In unipolar pacing, the pacing stimulation pulses are applied between a single electrode carried by the lead, in electrical contact with the desired heart chamber, and the pulse generator case. Usually the electrode serves as the cathode (negative pole) and the case serves as the anode (positive pole). In bipolar pacing, the pacing stimulation pulses are applied between a pair of closely spaced electrodes carried by the lead, in electrical contact with the desired heart chamber, one electrode serving as the anode and the other electrode serving as the cathode.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events represented as P waves on the surface electrocardiogram (ECG) and intrinsic ventricular events represented as R waves on the surface ECG. The pacemaker, however, does not use the surface ECG electrical events but uses the signal as identified inside the heart. This is termed an electrogram. It would be an atrial EGM (AEGM) for the native atrial depolarization and a ventricular EGM (VEGM) for a native ventricular depolarization. By monitoring such AEGM and VEGM, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses the same chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

The energies of the applied pacing pulses are selected to be above the pacing energy stimulation threshold of the respective heart chamber to cause the heart muscle of that chamber to depolarize or contract. If an applied pacing pulse has an energy below the pacing energy stimulation threshold of the respective chamber, the pacing pulse will be ineffective in causing the heart muscle of the respective chamber to depolarize or contract. As a result, there will be failure in sustaining the pumping action of the heart. It is therefore necessary to utilize applied pacing pulse energies which are assured of being above the pacing energy stimulation threshold. Similarly, event sensing thresholds are set to assure the intrinsic events, such as R waves and P waves are detected.

It is desirable to employ pacing energies which are not exorbitantly above the stimulation threshold. The reason for this is that pacemakers are implanted devices and rely solely on battery power. Using pacing energies that are too much above the stimulation threshold would result in early depletion of the battery and hence premature device replacement. Similarly, it is desirable to not render intrinsic event sensing sensitivities too sensitive to avoid sensing noise and other artifacts as the desired intrinsic events.

Operating parameters, such as capture and sensing thresholds are assessed at device implant and periodic follow-up visits with the physician. These processes may be automated. However, very often, atrial capture threshold, ventricular capture threshold, atrial sensing threshold and ventricular sensing threshold evaluation procedures are performed manually by the physicians. During these evaluations, changes in the electrogram signal and/or event markers generated from the electrogram signals are observed and the capture and/or sense thresholds are determined accordingly by the physician. Unfortunately, the changes in the electrogram signals or event markers sometimes can be subtle and the human reaction can be slow to react to them and hence be inaccurate. Some undesirable scenarios may result. These may include, for example, prolonged loss of ventricular capture without ventricular intrinsic support during a ventricular capture threshold test, prolonged loss of atrial capture without atrial intrinsic support during an atrial capture test, incorrect identification of ventricular capture threshold, incorrect identification of atrial capture threshold, missing a true intrinsic event that causes the improper delivery of a pacing pulse, potentially during a vulnerable refractory period, during an atrial or ventricular sensitivity test and incorrect identification of an atrial sensing threshold or a ventricular sensing threshold. Any one of the forgoing would be accompanied by undesirable consequences.

The present invention addresses these an other issues. More particularly, the present invention provides assistance to medical personnel during manual capture threshold and sense threshold evaluations.

SUMMARY OF THE INVENTION

According to one embodiment, the invention provides a system for verifying the occurrence of a cardiac event during a manual evaluation of an operating parameter of an implantable cardiac stimulation device. The system comprises a template generator that generates an electrogram template standard characterizing the cardiac event, an event marker pattern generator that generates a marker pattern standard representing a desired sequence of cardiac events including the cardiac event, and a sensing circuit that senses cardiac activity to provide an evaluation electrogram signal responsive to evaluation of the operating parameter. The template generator generates an evaluation electrogram from the evaluation electrogram signal and the event marker pattern generator generates an evaluation marker pattern from the evaluation electrogram signal. The system further comprises a cardiac event verifier that compares the evaluation electrogram to the electrogram template standard and the evaluation marker pattern to the marker pattern standard and verifies the occurrence of the cardiac event when the evaluation electrogram matches the electrogram template standard and the evaluation marker pattern matches the marker pattern standard.

The cardiac event may be an evoked response and the operating parameter may be capture threshold. The system may further comprise a threshold determining circuit that determines the capture threshold. The cardiac event may be an intrinsic event and the operating parameter may be sensing threshold. The system may further comprise a sensing threshold determining circuit that determines the sensing threshold.

The implantable cardiac device may further comprise an event marker generator that generates event markers and the telemetry circuit may transmit the event markers to the event marker pattern generator of an external programmer.

Alternatively, the external programmer may comprise an event marker generator that generates event markers responsive to the evaluation electrogram signal transmitted by the telemetry circuit.

The external programmer may be programmable to provide any one of a first end option, a second end option, and a third end option. The first end option may consist of determining the operating parameter, displaying the determined operating parameter, and terminating the manual evaluation. The second end option may consist of determining the operating parameter and providing a perceptible warning. The third end option may consist of determining the operating parameter and displaying the determined operating parameter.

In another embodiment, a programmer is arranged to verify the occurrence of a cardiac event during a manual evaluation of an operating parameter of an implantable cardiac stimulation device. The programmer comprises a template generator that generates an electrogram template standard characterizing the cardiac event, a telemetry circuit that receives electrogram signals transmitted by the implantable cardiac stimulation device, the template generator generating an evaluation electrogram from a received evaluation electrogram signal, and a cardiac event verifier that compares the evaluation electrogram to the electrogram template standard and verifies the occurrence of the cardiac event when the evaluation electrogram matches the electrogram template standard. The external programmer is programmable to provide any one of a first end option, a second end option, and a third end option, wherein the first end option consists of determining the operating parameter, displaying the determined operating parameter, and terminating the manual evaluation, wherein the second end option consists of determining the operating parameter and providing a perceptible warning, and wherein the third end option consists of determining the operating parameter and displaying the determined operating parameter.

In a further embodiment, a programmer is arranged to verify the occurrence of a cardiac event during a manual evaluation of an operating parameter of an implantable cardiac stimulation device and comprises a template generator that generates an electrogram template standard characterizing the cardiac event, an event marker pattern generator that generates a marker pattern standard representing a desired sequence of cardiac events including the cardiac event, the template generator generating an evaluation electrogram from an evaluation electrogram signal received from the implantable cardiac stimulation device and the event marker pattern generator generating an evaluation marker pattern from event markers received from the implantable cardiac stimulation device, and a cardiac event verifier that compares the evaluation electrogram to the electrogram template standard and the evaluation marker pattern to the marker pattern standard to verify the occurrence of the cardiac event when the evaluation electrogram matches the electrogram template standard and the evaluation marker pattern matches the marker pattern standard.

In another embodiment, a method verifies the occurrence of a cardiac event during a manual evaluation of an operating parameter of an implantable cardiac stimulation device. The method comprises generating an electrogram template standard characterizing the cardiac event, generating a marker pattern standard representing a desired sequence of cardiac events including the cardiac event; sensing cardiac activity to provide an evaluation electrogram signal responsive to evaluation of the operating parameter, generating an evaluation electrogram from the evaluation electrogram signal, generating an evaluation marker pattern from the evaluation electrogram signal, comparing the evaluation electrogram to the electrogram template standard and the evaluation marker pattern to the marker pattern standard, and indicating the occurrence of the cardiac event when the evaluation electrogram matches the electrogram template standard and the evaluation marker pattern matches the marker pattern standard.

BRIEF DESCRIPTION OF THE DRAWINGS

Further features and advantages of the invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the exemplary embodiments of the invention that follows, like numerals or reference designators will be used to refer to like parts or elements throughout.

Figure 1:
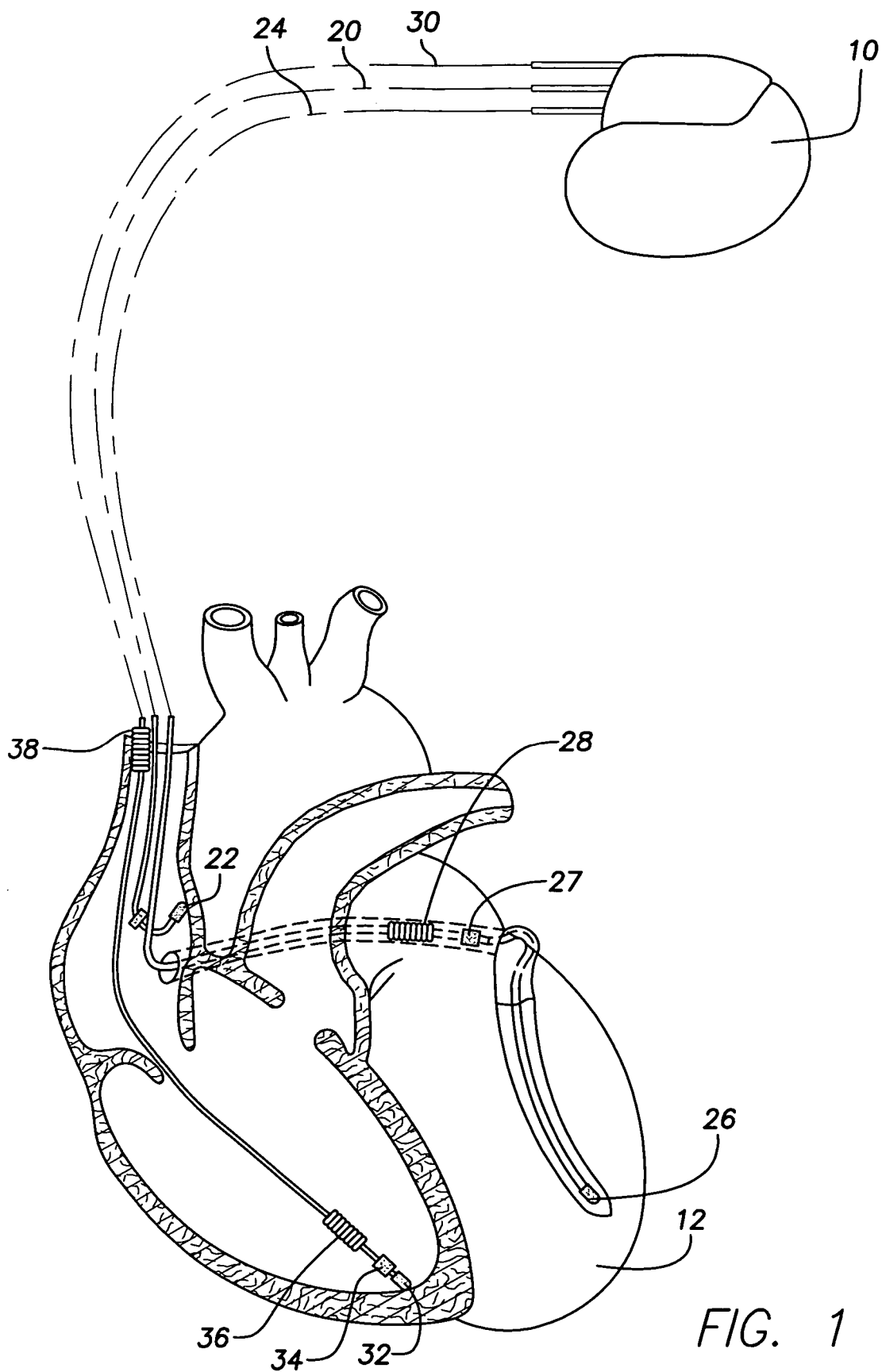
FIG. 1 is a simplified diagram illustrating an implantable stimulation device in electrical communication with at least three leads implanted into a patient's heart for delivering multi-chamber stimulation and shock therapy.
Figure 2:
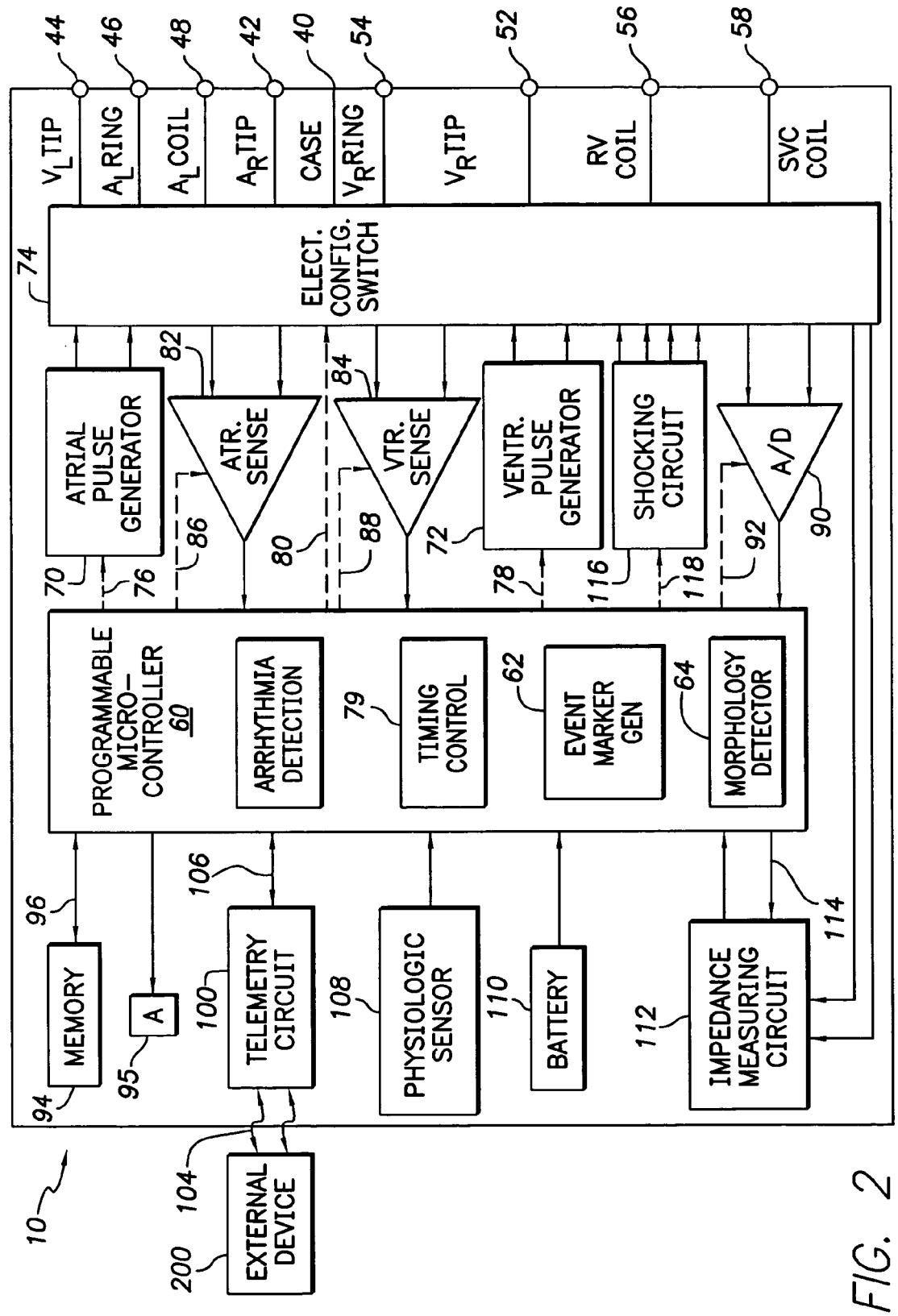
FIG. 2 is a functional block diagram of a multi-chamber implantable stimulation device illustrating the basic elements of a stimulation device, which can provide cardioversion, defibrillation and pacing stimulation in four chambers of the heart.
Figure 3:
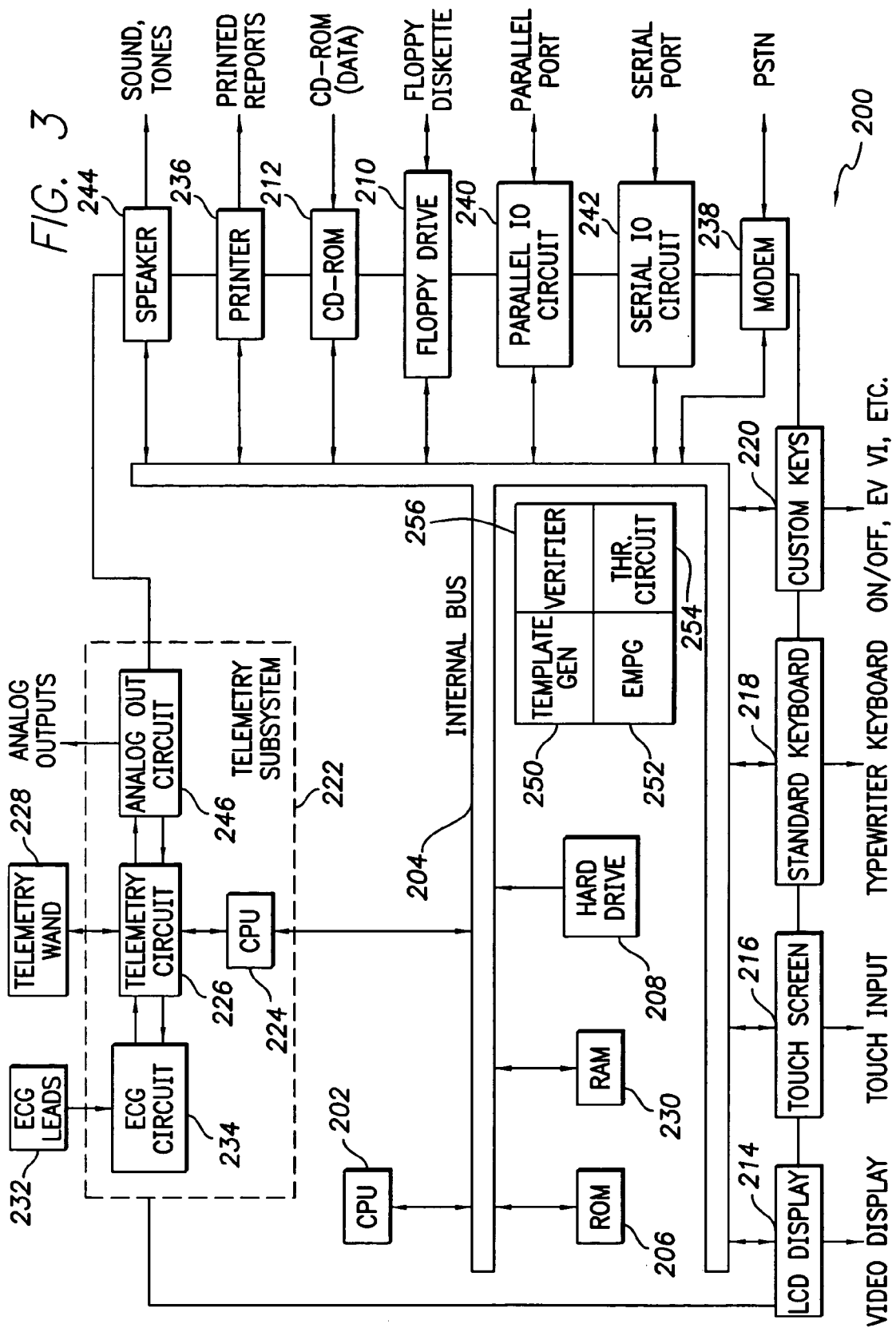
FIG. 3 is a functional block diagram illustrating components of a programmer for use in programming the implantable device of FIG. 1.

Initially, with reference to FIGS. 1-3, an overview of an exemplary implantable device and an exemplary device programmer are provided. Then a detailed description of two embodiments is provided with reference to the flow charts of FIGS. 4 and 5.

Implantable Stimulation Device

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. Pat. No. 5,466,254, "Coronary Sinus Lead with Atrial Sensing Capability" (Helland), which patent is hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

Representative types of control circuitry that may be used with the invention or modified for use with the invention include the microprocessor-based control system of U.S. Pat. No. 4,940,052 (Mann et al.), the state-machine of U.S. Pat. Nos. 4,712,555 (Thornander et al.) and 4,944,298 (Sholder). For a more detailed description of the various timing intervals used within the stimulation device and their inter-relationship, see U.S. Pat. No. 4,788,980 (Mann et al.). The '052, '555, '298 and '980 patents are incorporated herein by reference.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 84, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 200, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 200 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 that provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Device Programmer

FIG. 3 illustrates pertinent components of an external programmer 200 for use in programming an implantable medical device such as a pacemaker or ICD. Briefly, the programmer permits a physician or other user to program the operation of the implanted device and to retrieve and display information received from the implanted device such as IEGM data and device diagnostic data. Additionally, the external programmer receives and displays ECG data from separate external ECG leads that may be attached to the patient. Depending upon the specific programming of the external programmer, programmer 200 may also be capable of processing and analyzing data received from the implanted device and from the ECG leads to, for example, render preliminary diagnosis as to medical conditions of the patient or to the operations of the implanted device.

Now, considering the components of programmer 200, operations of the programmer are controlled by a CPU 202, which may be a generally programmable microprocessor or microcontroller or may be a dedicated processing device such as an application specific integrated circuit (ASIC) or the like. Software instructions to be performed by the CPU are accessed via an internal bus 204 from a read only memory (ROM) 206 and random access memory 230. Additional software may be accessed from a hard drive 208, floppy drive 210, and CD ROM drive 212, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 214 or other suitable computer display device. To this end, the CPU may, for example, display a menu of specific programming parameters of the implanted device to be programmed or may display a menu of types of diagnostic data to be retrieved and displayed. In response thereto, the physician enters various commands via either a touch screen 216 overlaid on the LCD display or through a standard keyboard 218 supplemented by additional custom keys 220, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Typically, the physician initially controls the programmer 200 to retrieve data stored within the implanted medical device and to also retrieve ECG data from ECG leads, if any, coupled to the patient. To this end, CPU 202 transmits appropriate signals to a telemetry subsystem 222, which provides components for directly interfacing with the implanted device, and the ECG leads. Telemetry subsystem 222 includes its own separate CPU 224 for coordinating the operations of the telemetry subsystem. Main CPU 202 of programmer communicates with telemetry subsystem CPU 224 via internal bus 204. Telemetry subsystem additionally includes a telemetry circuit 226 connected to a telemetry wand 228, which, in turn, receives and transmits signals electromagnetically from a telemetry unit of the implanted device. The telemetry wand is placed over the chest of the patient in the vicinity of the implanted device to permit reliable transmission of data between the telemetry wand and the implanted device. Typically, at the beginning of the programming session, the external programming device controls the implanted device via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the implanted device is stored by external programmer 200 either within a random access memory (RAM) 230, hard drive 208 or within a floppy diskette placed within floppy drive 210. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted device is transferred to programmer 200, the implanted device may be further controlled to transmit additional data in real time as it is detected by the implanted device, such as additional IEGM data, lead impedance data, and the like. Additionally, or in the alternative, telemetry subsystem 222 receives ECG signals from ECG leads 232 via an ECG processing circuit 234. As with data retrieved from the implanted device itself, signals received from the ECG leads are stored within one or more of the storage devices of the external programmer. Typically, ECG leads output analog electrical signals representative of the ECG. Accordingly, ECG circuit 234 includes analog to digital conversion circuitry for converting the signals to digital data appropriate for further processing within programmer. Depending upon the implementation, the ECG circuit may be configured to convert the analog signals into event record data for ease of processing along with the event record data retrieved from the implanted device. Typically, signals received from the ECG leads are received and processed in real time. See U.S. Pat. Nos. 4,596,255 and 4,791,936, by Snell et al., both entitled "Apparatus for Interpreting and Displaying Cardiac Events of a Heart Connected to a Cardiac Pacing Means."

Thus the programmer receives data both from the implanted device and from the external ECG leads. Data retrieved from the implanted device includes parameters representative of the current programming state of the implanted device. Under the control of the physician, the external programmer displays the current programming parameters and permits the physician to reprogram the parameters. To this end, the physician enters appropriate commands via any of the aforementioned input devices and, under control of CPU 202, the programming commands are converted to specific programming parameters for transmission to the implanted device via telemetry wand 228 to thereby reprogram the implanted device. Techniques for programming an implanted medical device may be found in U.S. Pat. No. 5,716,382 entitled "Programmer for an Implantable Cardiac Stimulating Device." Prior to reprogramming specific parameters, the physician may control the external programmer to display any or all of the data retrieved from the implanted device or from the ECG leads, including displays of ECGs, IEGMs, and statistical patient information. Further information pertaining to the types of information which may be displayed using programmer may be found in U.S. Pat. No. 5,974,341 entitled "Method and Apparatus for Detecting and Displaying Diagnostic Information in Conjunction with Intracardiac Electrograms and Surface Electrocardiograms." Any or all of the information displayed by programmer may also be printed using a printer 236.

Programmer 200 also includes a modem 238 to permit direct transmission of data to other programmers via the public switched telephone network (PSTN) or other interconnection line, such as a T1 line or fiber optic cable. Depending upon the implementation, the modem may be connected directly to internal bus 204 may be connected to the internal bus via either a parallel port 240 or a serial port 242. Other peripheral devices may be connected to the external programmer via parallel port 240 or a serial port 242 as well. Although one of each is shown, a plurality of input output (IO) ports may be provided.

A speaker 244 is included for providing audible tones to the user, such as a warning beep in the event improper input is provided by the physician. Telemetry subsystem 222 additionally includes an analog output circuit 246 for controlling the transmission of analog output signals, such as IEGM signals output to an ECG machine or chart recorder.

With the programmer configured as shown, a physician or other user operating the external programmer is capable of retrieving, processing and displaying a wide range of information received from the ECG leads or from the implanted device and to reprogram the implanted device if needed. The descriptions provided herein with respect to FIG. 3 are intended merely to provide an overview of the operation of programmer and are not intended to describe in detail each and every feature of the hardware and software of the device and is not intended to provide an exhaustive list of the functions performed by the device.

Now that a general description of the device 10 and programmer 200 has been provided, the description shall now turn to those elements that more directly relate to an embodiment of the present invention. The invention may be employed during operating parameter assessment, such as for both capture threshold testing and sense threshold testing. In its broader aspects, the invention may be employed to measure the changes in the electrogram (IEGM) signal and an event marker sequence related to the pacing pulse/sensing event. At the in-clinic environment during the short time of the capture/sensing threshold testing, the evoked responses of the heart are very similar and the intrinsic activities are relatively stable. Therefore, a pattern matching technique may be employed for the morphology pattern as well as the marker sequence to determine if a stimulus captures the heart, (both for atrium and ventricle), and to determine if the system senses intrinsic events. The capture test may start with a current pacing amplitude or an amplitude representing a 2:1 safety margin to assure capture of the heart tissue. The system acquires an evoked response template and a marker sequence template at the beginning of the test and then compares them to the data collected with subsequent stimuli of decreasing amplitudes. A change of IEGM waveform morphology or marker sequence is then noted and used to inform the user that a loss of capture is occurring. The user can respond easily and quickly to this processed information and make a quick decision. The system can also terminate the test upon a predefined condition if the system has been so programmed. As will be seen hereinafter, at least three different end points are possible: (1) the system automatically determines the threshold and terminates the test when the threshold is determined; (2) the system determines the threshold and issues a warning to the user that the threshold is determined and to permit the customer to terminate the test; and (3) the system determines the threshold just for reference.

To these ends, it will be noted that the device 10 shown in FIG. 1 includes an event marker generator 62. The event marker generator 62 generates event markers responsive to the detection of both R waves and P waves as well as ventricular and atrial evoked responses. The markers are then transmitted to the programmer 200 by the telemetry circuit 100 for use by an event marker pattern generator (EMPG) 252 of the programmer 200 (FIG. 3) in generating marker pattern standards representing desired sequences of cardiac events including the events to be verified.

Similarly, the morphology detector isolates discrete IEGM portions of the electrogram signals generated by the data acquisition system 90 and transmits the electrogram portions to the programmer. A template generator 250 of the programmer 200 uses the received IEGM portions to generate an electrogram template standard with respect to each cardiac event to be verified. The IEGM portions preferably begin just prior to the desired event and terminates just after the desired event.

Once the electrogram template standards and marker pattern standards are generated, the system is prepared to assist in manual evaluations. When an evaluation of a pacing parameter has begun, the data acquisition system 90 senses cardiac activity and provides an evaluation electrogram signal. The event marker generator generates event markers from the evaluation electrogram signal. The markers are then transmitted to the programmer 200 where the EMPG 252 generates an evaluation marker pattern. The cardiac event verifier then compares the evaluation electrogram to the electrogram template standard and the evaluation marker pattern to the marker pattern standard. If they both match, the occurrence of the particular cardiac event is verified. The cardiac event may, for example, be an existence of an evoked response and the pacing parameter may be capture threshold. The programmer 200 further includes a threshold determining circuit 254 that determines, at the end of the test, the capture threshold. Alternatively, the cardiac event may be an intrinsic event such as an R wave or a P wave. Here the pacing parameter would be sensing threshold. The threshold determining circuit may be employed to determine the sensing threshold upon completion of the sensing threshold test.

Figure 4:
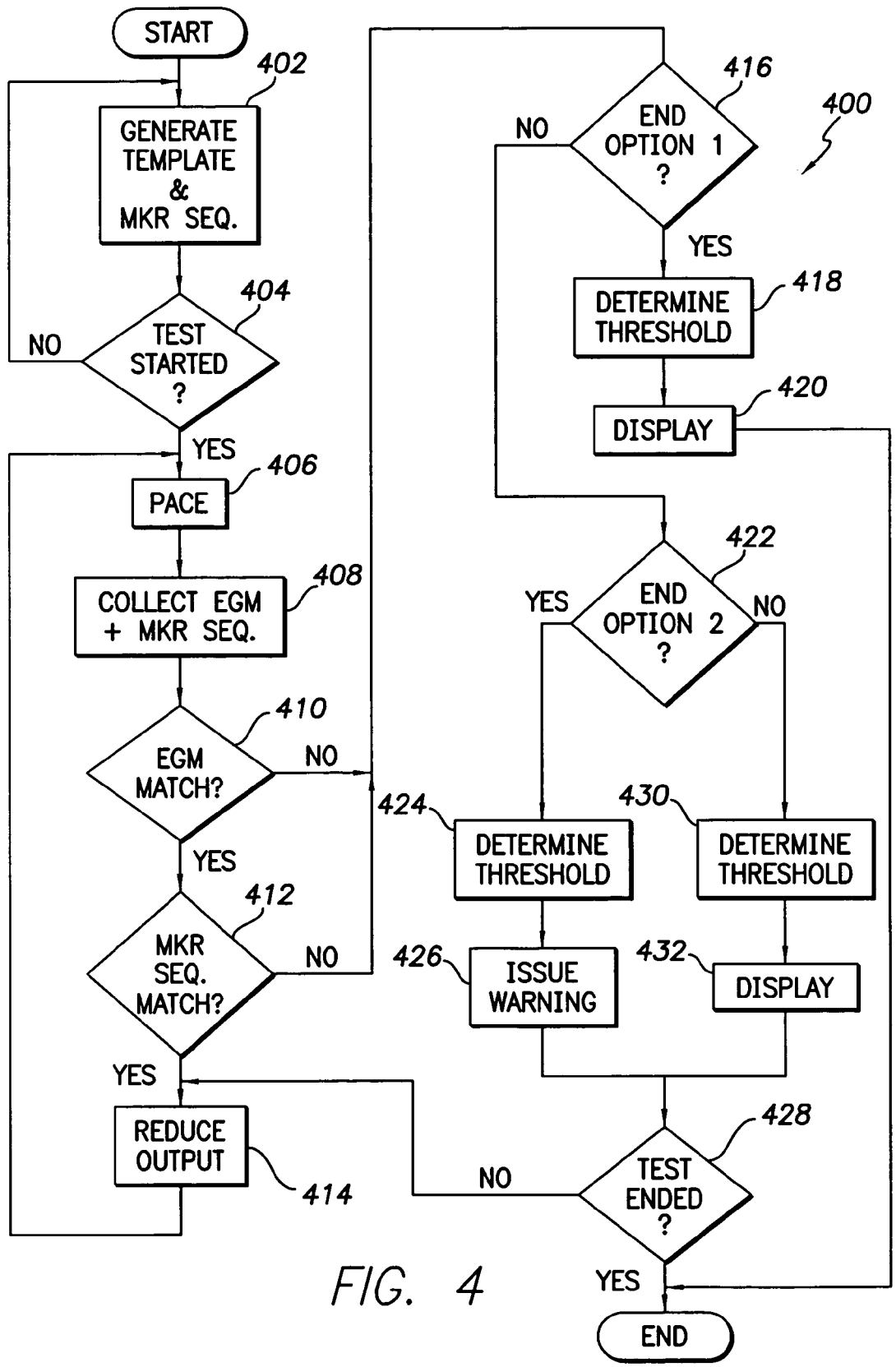
FIG. 4 is a flow chart illustrating the overall operation of an embodiment of the invention that verifies the occurrence of cardiac events during a capture threshold evaluation.

Referring now to FIG. 4, it shows a flow diagram 400 describing one embodiment of the invention for assisting in a capture threshold manual evaluation. The process of FIG. 4 initiates with activity block 402 wherein the electrogram template standard and marker pattern standard are generated. Then, in decision block 404, it is determined if the capture threshold manual test has begun. If not, the process returns to update the electrogram template standard and the marker pattern standard. If the manual test has begun, the system delivers (or waits for the delivery of) a pacing pulse in activity block 406. Then, in activity block 408, the evaluation electrogram is collected along with its marker sequence. Next, in decision block 410, the verifier 256 determines if the evaluation electrogram matches the electrogram template standard. If it does, the process continues to decision block 412 to determine if the evaluation marker pattern matches the marker pattern standard. If it does, the process then proceeds to activity block 414 where the stimulation output is incrementally decreased for the next pacing pulse. The process then returns to activity block 406 for the next pacing pulse.

If in either decision block 410 or 412 it is determined that there in no match (the subject evoked response did not occur), the process advances to decision block 416 to determine if the first end option has been selected. If it has, the process advances to activity block 418 where the threshold circuit 254 determines the capture threshold. The threshold results are then displayed in accordance with activity block 420 and the process exits.

If in decision block 416 it is determined that the first end option is not selected, the process advances to decision block 422 where it is determined if the second end option is selected. If it is, the process advances to activity block 424 where the capture threshold is determined by threshold circuit 254. A warning is then issued by an alarm 95 of device 10 (FIG. 2). The alarm may be, for example, a transducer that vibrates to provide an auditory perceptible indication that the threshold has been determined. The process then advances to decision block 428 to determine if the user wants the test to end. If the user terminates the test, the process completes. If the test is not terminated, the process returns to activity block 414.

If in decision block 422 it is determined that the second end option is not selected meaning that the third end option is selected, the process advances to activity block 424 where the capture threshold is determined by threshold circuit 254. The determined capture threshold is then displayed for reference. The process then advances to decision block 428 to determine if the user wants the test to end. If the user terminates the test, the process completes. If the test is not terminated, the process returns to activity block 414.

Figure 5:
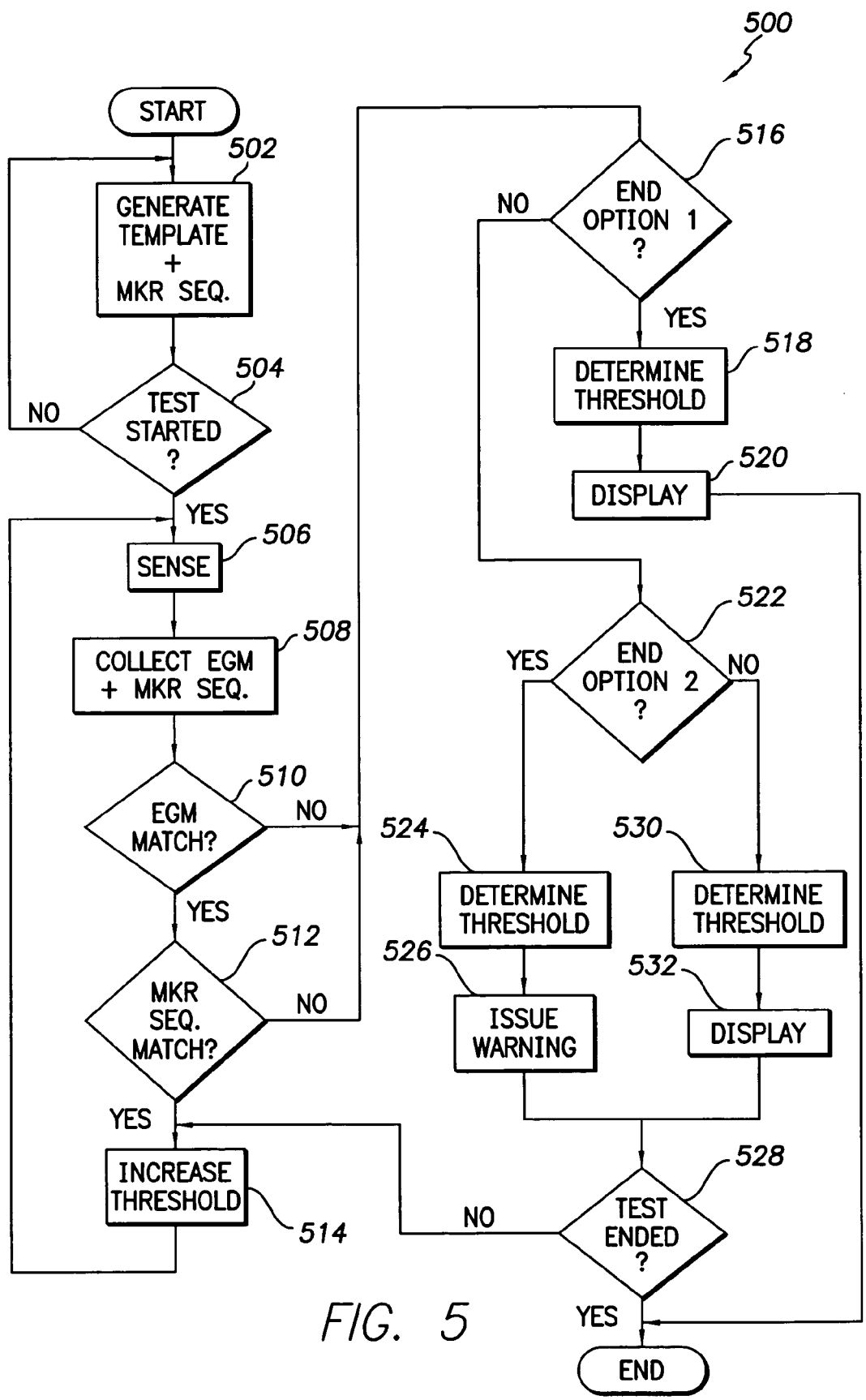
FIG. 5 is a flow chart illustrating the overall operation of an embodiment of the invention that verifies the occurrence of cardiac events during a sensing threshold evaluation.

Referring now to FIG. 5, it shows a flow diagram 500 describing one embodiment of the invention for assisting in a sensing threshold manual evaluation. The process of FIG. 5 initiates with activity block 502 wherein the electrogram template standard and marker pattern standard are generated. Then, in decision block 504, it is determined if the sensing threshold manual test has begun. If not, the process returns to update the electrogram template standard and the marker pattern standard. If the manual test has begun, the system senses cardiac activity during a sensing period corresponding to the time that the intrinsic event, such as an R wave or a P wave, is due to occur in activity block 506. Then, in activity block 508, the resulting evaluation electrogram is collected along with its marker sequence. Next, in decision block 510, the verifier 256 determines if the evaluation electrogram matches the electrogram template standard. If it does, the process continues to decision block 512 to determine if the evaluation marker pattern matches the marker pattern standard. If it does, the process then proceeds to activity block 514 where the sense threshold is incrementally increased (sensitivity decreased) for the next sensing period. The process then returns to activity block 506 for the next sensing period.

If in either decision block 510 or 512 it is determined that there in no match (the subject intrinsic event was not sensed), the process advances to decision block 516 to determine if the first end option has been selected. If it has, the process advances to activity block 418 where the threshold circuit 254 determines the sensing threshold. The threshold results are then displayed in accordance with activity block 420 and the process exits.

If in decision block 516 it is determined that the first end option is not selected, the process advances to decision block 522 where it is determined if the second end option is selected. If it is, the process advances to activity block 524 where the sensing threshold is determined by threshold circuit 254. A warning is then issued by an alarm 95 of device 10 (FIG. 2). The alarm may be, for example, a transducer that vibrates to provide an auditory perceptible indication that the sensing threshold has been determined. The process then advances to decision block 528 to determine if the user wants the test to end. If the user terminates the test, the process completes. If the test is not terminated, the process returns to activity block 514.

If in decision block 522 it is determined that the second end option is not selected meaning that the third end option is selected, the process advances to activity block 524 where the sensing threshold is determined by threshold circuit 254. The determined capture threshold is then displayed for reference. The process then advances to decision block 528 to determine if the user wants the test to end. If the user terminates the test, the process completes. If the test is not terminated, the process returns to activity block 514.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. A system for verifying the occurrence of a cardiac event during a manual evaluation of an operating parameter of an implantable cardiac stimulation device, comprising:
   a template generator that generates an electrogram template standard characterizing the cardiac event;
   an event marker pattern generator that generates a marker pattern standard representing a desired sequence of cardiac events including the cardiac event;
   a sensing circuit that senses cardiac activity to provide an evaluation electrogram signal responsive to evaluation of the operating parameter,
   the template generator generating an evaluation electrogram from the evaluation electrogram signal,
   the event marker pattern generator generating an evaluation marker pattern from the evaluation electrogram signal, and
   a cardiac event verifier that compares the evaluation electrogram to the electrogram template standard and the evaluation marker pattern to the marker pattern standard and verifies the occurrence of the cardiac event when the evaluation electrogram matches the electrogram template standard and the evaluation marker pattern matches the marker pattern standard.

2. The system of claim 1, wherein the cardiac event is an evoked response and the operating parameter is capture threshold.

3. The system of claim 1, wherein the cardiac event is an intrinsic event and the operating parameter is sensing threshold.

4. The system of claim 1, wherein the cardiac event is an evoked response, the operating parameter is capture threshold, and wherein the system further comprises a threshold determining circuit that determines the capture threshold.

5. The system of claim 1, wherein the cardiac event is an intrinsic event, the operating parameter is sensing threshold, and wherein the system further comprises a sensing threshold determining circuit that determines the sensing threshold.

6. The system of claim 1, further comprising an external programmer and wherein the external programmer includes the template generator, the event marker pattern generator, and the cardiac event verifier.

7. The system of claim 6, wherein the implantable cardiac device includes the sensing circuit and further comprises a telemetry circuit that transmits the evaluation electrogram signal to the external programmer.

8. The system of claim 7, wherein the implantable cardiac device further comprises an event marker generator that generates event markers and wherein the telemetry circuit transmits the event markers to the event marker pattern generator of the external programmer.

9. The system of claim 7, wherein the external programmer further comprises an event marker generator that generates event markers responsive to the evaluation electrogram signal transmitted by the telemetry circuit.

10. The system of claim 1, further comprising an external programmer and wherein the external programmer includes the template generator, the event marker pattern generator, and the cardiac event verifier, and wherein the external programmer is programmable to provide any one of a first end option, a second end option, and a third end option, wherein the first end option consists of determining the operating parameter, displaying the determined operating parameter, and terminating the manual evaluation, wherein the second end option consists of determining the operating parameter and providing a perceptible warning, and wherein the third end option consists of determining the operating parameter and displaying the determined operating parameter.

11. A programmer arranged to verify the occurrence of a cardiac event during a manual evaluation of an operating parameter of an implantable cardiac stimulation device, comprising:

a template generator that generates an electrogram template standard characterizing the cardiac event;

an event marker pattern generator that generates a marker pattern standard representing a desired sequence of cardiac events including the cardiac event, the template generator generating an evaluation electrogram from an evaluation electrogram signal received from the implantable cardiac stimulation device, the event marker pattern generator generating an evaluation marker pattern from event markers received form the implantable cardiac stimulation device, and a cardiac event verifier that compares the evaluation electrogram to the electrogram template standard and the evaluation marker pattern to the marker pattern standard and verifies the occurrence of the cardiac event when the evaluation electrogram matches the electrogram template standard and the evaluation marker pattern matches the marker pattern standard.

12. The programmer of claim 11, wherein the cardiac event is an evoked response and the operating parameter is capture threshold.

13. The programmer of claim 11, wherein the cardiac event is an intrinsic event and the operating parameter is sensing threshold.

14. The programmer of claim 11, wherein the cardiac event is an evoked response, the operating parameter is capture threshold, and wherein the system further comprises a threshold determining circuit that determines the capture threshold.

15. The programmer of claim 11, wherein the cardiac event is an intrinsic event, the operating parameter is sensing threshold, and wherein the system further comprises a sensing threshold determining circuit that determines the sensing threshold.

16. The programmer of claim 11, further comprising a telemetry circuit that receives the evaluation electrogram signal from the implantable cardiac stimulation device.

17. The programmer of claim 11, further comprising a telemetry circuit that receives the event markers from the implantable cardiac stimulation device.

18. A method of verifying the occurrence of a cardiac event during a manual evaluation of an operating parameter of an implantable cardiac stimulation device, comprising:

generating an electrogram template standard characterizing the cardiac event;

generating a marker pattern standard representing a desired sequence of cardiac events including the cardiac event;

sensing cardiac activity to provide an evaluation electrogram signal responsive to evaluation of the operating parameter;

generating an evaluation electrogram from the evaluation electrogram signal;

generating an evaluation marker pattern from the evaluation electrogram signal;

comparing the evaluation electrogram to the electrogram template standard and the evaluation marker pattern to the marker pattern standard; and indicating the occurrence of the cardiac event when the evaluation electrogram matches the electrogram template standard and the evaluation marker pattern matches the marker pattern standard.

19. The method of claim 18, wherein the cardiac event is an evoked response and the operating parameter is capture threshold.

20. The method of claim 18, wherein the cardiac event is an intrinsic event and the operating parameter is sensing threshold.

* * * * *

UNITED STATES PATENT AND TRADEMARK OFFICE
CERTIFICATE OF CORRECTION

| | | |
|---|---|---|
| PATENT NO. | : 7,587,243 B1 | Page 1 of 1 |
| APPLICATION NO. | : 11/430785 | |
| DATED | : September 8, 2009 | |
| INVENTOR(S) | : Xing Pei | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 793 days.

Signed and Sealed this

Twenty-first Day of September, 2010

David J. Kappos
*Director of the United States Patent and Trademark Office*